US006423325B1

(12) United States Patent
Alaluf et al.

(10) Patent No.: US 6,423,325 B1
(45) Date of Patent: Jul. 23, 2002

(54) SKIN CARE COMPOSITION

(75) Inventors: Simon Alaluf, Bedford; Anthony Vincent Rawlings, Bebington, both of (GB)

(73) Assignee: Conopco, Inc., New York, NY (US)

( * ) Notice: Subject to any disclaimer, the term of this patent is extended or adjusted under 35 U.S.C. 154(b) by 0 days.

(21) Appl. No.: 09/627,596

(22) Filed: Jul. 28, 2000

(30) Foreign Application Priority Data

Jul. 30, 1999 (GB) ............................................ 9918023

(51) Int. Cl.⁷ .......................... A61K 7/00; A61K 31/20
(52) U.S. Cl. ........................ 424/401; 514/558; 514/844
(58) Field of Search .......................... 424/401; 514/558, 514/844

(56) References Cited

U.S. PATENT DOCUMENTS

| | | | | |
|---|---|---|---|---|
| 5,252,333 A | * | 10/1993 | Horrobin | 424/422 |
| 5,562,913 A | | 10/1996 | Horrobin | 424/401 |
| 5,620,701 A | * | 4/1997 | Horrobin et al. | 424/443 |
| 5,679,809 A | * | 10/1997 | Bertoli et al. | 554/186 |
| 6,077,520 A | * | 6/2000 | Tominaga | 424/401 |
| 6,133,463 A | | 10/2000 | Fourneron et al. | 554/79 |
| 6,139,852 A | * | 10/2000 | Takeoka et al. | 424/401 |

FOREIGN PATENT DOCUMENTS

| | | | |
|---|---|---|---|
| EP | 116 439 | | 8/1984 |
| EP | 304 603 | | 3/1989 |
| EP | 615 753 | | 9/1994 |
| EP | 640 581 | | 3/1995 |
| EP | 659 755 | | 6/1995 |
| EP | 709 084 | | 5/1996 |
| EP | 888 773 | | 1/1999 |
| FR | 2 648 347 | | 12/1990 |
| GB | 2 202 146 A | * | 9/1988 |
| GB | 2 202 146 | | 9/1988 |
| GB | 2 217 602 | | 11/1989 |
| JP | 04026610 A2 | * | 1/1992 |
| JP | 05/271046 | | 10/1993 |
| JP | 05279240 A2 | * | 10/1993 |
| JP | 05279241 A2 | * | 10/1993 |
| JP | 05286845 A2 | * | 11/1993 |
| JP | 05286846 A2 | * | 11/1993 |
| JP | 09087686 A2 | * | 3/1997 |
| JP | 09291021 A2 | * | 11/1997 |
| KR | 9602176 B1 | * | 2/1996 |
| WO | 96/37200 | | 11/1996 |
| WO | 99/47110 | | 9/1999 |
| WO | 00/15179 | | 3/2000 |

OTHER PUBLICATIONS

Great Britain Search Report in a GB application 9918023.4., 12/99.
Lavker, R.J. Inv. Derm., (1979), 73, 79–66.
Griffiths et al. N. Engl. J. med (1993) 329, 530–535.
Kliewer et al. 1992 Nature, 358, 771–774.
PCT International Search Report in a PCT application PCT/EP 00/06598, Nov. 2000.
Derwent Abstract XP 002152331, 1974.
Derwent Abstract XP 002152332, 1999.

* cited by examiner

*Primary Examiner*—Jose G. Dees
*Assistant Examiner*—Marina Lamm
(74) *Attorney, Agent, or Firm*—Ellen Plotkin

(57) ABSTRACT

A topical composition comprising:

(a) a first lipid selected from petroselinic acid and/or docosahexaenoic acid and/or derivatives thereof;

(b) a second lipid which is an activator of peroxisome proliferator activated receptors sub-type alpha and/or derivatives thereof and/or mixtures thereof; and (c) a dermatologically acceptable vehicle; with the proviso that the first and second lipids are not the same lipid. The compositions are useful as cosmetic anti-ageing skin care creams and lotions.

5 Claims, No Drawings

SKIN CARE COMPOSITION

FIELD OF THE INVENTION

This invention relates to topical compositions for application to human skin and to their use in improving the condition and appearance of skin.

BACKGROUND OF THE INVENTION

Skin is subject to deterioration through dermatological disorders, environmental abuse (wind, air conditioning, central heating) or through the normal ageing process (chronoageing) which may be accelerated by exposure of skin to sun (photoageing). In recent years the demand for cosmetic methods for improving the appearance and condition and, in particular, for reversing, reducing or preventing the visible signs of wrinkled, aged and/or photodamaged skin has grown enormously.

Consumers are increasingly seeking "anti-ageing" cosmetic products that reverse, treat or delay the visible signs of chronoaging and photoaging skin such as wrinkles, lines, sagging, hyperpigmentation and age spots.

Collagen, the predominant matrix skin protein is known to impart tensile strength to skin. It is also known in the art that the levels of collagen in skin are significantly reduced with aged and/or photodamaged skin. Many studies have shown that the levels of collagen type I in skin is decreased with age and/or with increased photodamage, (for example Lavker, R. J.Inv.Derm., (1979), 73, 79–66; Griffiths et al. N. Eng. J. med.(1993) 329, 530–535. The reduction of the levels of collagen in skin is accordingly associated with a decrease in the tensile strength of the skin causing wrinkles and laxity.

It is well known in the art that retinoic acid is a potent anti-ageing active and induces dermal repair of photodamaged skin. It has been shown that wrinkle effacement and dermal repair following topical treatment of skin with retinoic acid arises through new collagen deposition and synthesis in the skin (for example, Griffiths et al. N. Eng. J. med. (1993) 329, 530–535). It is widely accepted that strengthening of the dermal matrix by boosting the level of collagen in skin using retinoic acid provides anti-ageing/dermal repair benefits.

J05271046 describes a skin composition that contains an unsaturated fatty acid having 18 to 22 carbons and two or more unsaturated bonds, such as linoleic and arachidonic acid and a polyphenol. This composition is useful for lightening the skin.

Use of oils rich in petroselinic acid in skin care compositions as a moisturising agent has been described in EP A 0709084.

The use of fatty acids, including petroselinic acid, in cosmetic formulations for treating the hair is known. EP-A-116439 describes hair tonics, which include fatty acids, such as petroselinic acid, linoleic acid, linolenic acid oleic acid and arachidonic acid for alleviating dandruff and for stimulating hair growth.

We have now found that effective treatment and prevention of normal, but cosmetically undesirable, skin conditions, due to chronoaging or photoaging, such as wrinkles, lines, sagging, hyperpigmentation and age spots, may be obtained through the application of cosmetic compositions to the skin which comprises a specific combination of two lipid components.

The art discussed above does not disclose the specific synergistic combination of a first lipid component selected from petroselinic acid or docosahexaenoic acid together with a second lipid component, nor the use of such a specific combination for treating ageing skin.

SUMMARY OF THE INVENTION

According to a first aspect of the present invention there is provided a topical composition comprising:

(a) a first lipid component selected from petroselinic acid and/or docosahexaenoic acid and/or derivatives thereof;

(b) a second lipid component which is an activator of peroxisome proliferator activated receptors of sub-type alpha and/or derivatives thereof and/or mixtures thereof; and (c) a dermatologically acceptable vehicle.

According to a second aspect of the present invention there is provided a cosmetic method of providing at least one skin care benefit selected from: treating/preventing wrinkling, sagging, dry, aged and/or photodamaged skin; boosting collagen deposition in skin, boosting decorin production in skin, enhancing tissue repair; improving skin texture, smoothness and/or firmness; the method comprising applying to the skin a topical composition as described above.

The present invention also encompasses the use of the inventive compositions for providing at least one skin care benefit selected from treating/preventing wrinkling, sagging, aged and/or photodamaged skin; boosting collagen deposition in skin, boosting decorin production in skin, enhancing tissue repair; and improving skin texture, smoothness and/or firmness.

According to a still further aspect of the present invention there is provided the use of a first lipid component selected from petroselinic acid and/or docosahexaenoic acid and/or derivatives thereof in combination with a second lipid component which is an activator of the peroxisome proleferator activated receptor sub-type alpha and/or derivatives thereof and/or mixtures thereof in a cosmetic topical composition for providing at least one cosmetic skin care benefit selected from treating/preventing wrinkling, sagging, aged and/or photodamaged skin; boosting collagen deposition in skin, boosting decorin production in skin, enhancing tissue repair; and improving skin texture, smoothness and/or firmness.

The inventive compositions, methods and uses thus provide anti-ageing benefits which result in the promotion of smooth and supple skin with improved elasticity and a reduced or delayed appearance of wrinkles and aged skin, with improved skin colour. A general improvement in the appearance, texture and condition, in particular with respect to the radiance, clarity, and general youthful appearance of skin is achieved.

The term "treating" as used herein includes within its scope reducing, delaying and/or preventing the above mentioned normal, but cosmetically undesirable, skin conditions caused by the normal ageing process. The visible signs of aging, such as wrinkles, lines and/or sagging are delayed or reduced. Generally, the quality of skin is enhanced and its appearance and texture is improved by preventing or reducing wrinkling and increasing flexibility, firmness, smoothness, suppleness and elasticity of the skin. The compositions, methods and uses according to the invention may be useful for treating skin that is already in a wrinkled, aged, and/or photodamaged condition or for treating youthful skin to prevent or reduce those aforementioned undesirable changes due to the normal ageing/photoageing process.

DETAILED DESCRIPTION OF THE INVENTION

Petroselinic Acid and Docosahexaenoic Acid

Petroselinic acid (hereinafter referred to as PA) is a monounsaturated long chain (C18) fatty acid, having the formula $CH_3(CH_2)_{10}CH=CH(CH_2)_4COOH$.

Docosahexaenoic acid (hereinafter referred to as DHA) is a polyunsaturated long chain ($C_{22}$) fatty acid having the formula $CH_3(CH_2CH=CH)_6CH_2CH_2COOH$.

The invention also includes derivatives of the free acid which thus comprise petroselinic acid/docosahexaenoic acid moieties. Preferable derivatives include those derived from substitution of the carboxyl group of the acid, such as esters (e.g. triglyceride esters, monoglyceride esters, diglyceride esters, phosphoesters), amides (e.g. ceramide derivatives), salts (e.g. alkali metal and alkali earth metal salts, ammonium salts); and/or those derived from substitution of the $C18/C_{22}$ carbon chain, such as alpha hydroxy and/or beta hydroxy derivatives.

In the case of triglyceride ester derivatives, all positional isomers of PA/DHA substituents on the glycerol backbone are included. The triglycerides must contain at least one PA/DHA moiety. For example, of the three esterifiable positions on the glycerol backbone, the 1 and 2 positions may be esterified with PA/DHA and by another lipid at position 3 or as an alternative, the glycerol backbone could be esterified by PA/DHA at the 1 and 3 positions with another lipid at position 2.

Oils that are rich in petroselinic acid triglyceride are thus also suitable for use in the present invention. Such oils are commercially available and include parsley seed oil, carrot seed oil, fennel fruit oil, parsnip seed oil, coriander seed oil, chervil seed oil, caraway plant oil, and celery seed oil.

Oils that are rich in the DHA triglyceride are also suitable for use in the present invention. Such oils are commercially available and include fish oils and their concentrates.

Wherever the term "petroselinic acid" or "PA" or "docosahexaenoic acid" or "DHA" is used in this specification it is to be understood that the derivatives thereof comprising PA/DHA moieties are also included. "PA/DHA moieties" refers to PA/DHA fatty acyl portion(s) of a PA/DHA derivative.

The PA and or DHA to be employed in accordance with the present invention is present in the topical composition in an effective amount. Normally the total amount of the active is present in an amount between 0.0001% and 50% by weight of the composition. More preferably the amount is from 0.01% to 10% and most preferably from 0.1% to 5% in order to maximise benefits at a minimum cost. Where the first lipid is DHA or a DHA derivative, preferably it is present at a level of less than 3% by weight to avoid any potential odour problems.

Lipid Activators of Peroxisome Proliferator Activated Receptors of Sub-Type α

The term "activator of peroxisome proliferator activated receptors of sub-type α" or "PPAR α activator" in the present application means a lipid that activates the nuclear receptor PPAR α.

Peroxisome proliferator activated receptors are a known family of nuclear hormone receptors having three subtypes, α, β, γ, of varying tissue distribution. Peroxisome proliferator activated receptors subtype α (hereinafter referred to as PPAR α) are present in skin. Lipid activators of PPAR α such as linoleic acid are well known in the art. These have been shown to accelerate skin epidermal barrier development in vitro (Hanley et al,(1997) J.Clin.Inv 100,705–712). However, there is no disclosure or suggestion in the art of activators of PPAR α having use in cosmetic compositions for providing cosmetic anti-ageing treatments.

An established and widely accepted method by which PPAR activation can be demonstrated and thus by which lipid activators of PPARs can be identified is the reporter gene assay. Lipids that are activators of PPAR α are thus easily identifiable by those skilled in the art as those compounds which cause expression of luciferase or chloramphenicol acetyl transferase (hereinafter referred to as CAT) in the reporter gene assay outlined in Example 1 below—the full protocol is provided by Kliewer et al. (1992) Nature, 358, 771–774.

Thus if a lipid compound passes this in vitro reporter gene assay, that is it causes expression of luciferase or CAT in the reporter gene assay outlined in Example 1 below, it is included as a lipid PPAR α activator even if it is not specifically mentioned herein. In a preferred embodiment of the invention, the lipid PPAR α activator is a compound which promotes activation of the reporter gene at least 2-fold above background levels as these are the more effective anti-ageing agents.

Examples of lipid PPAR α activators which satisfy the reporter gene assay test include C10–C18 saturated fatty acids which preferably are branched, or preferably derivatised (eg with hydroxy groups) if straight chain, C10–C20 monounsaturated fatty acids and C10–C22 polyunsaturated fatty acids.

The fatty acids may be straight or branched chain, saturated or unsaturated and may be substituted e.g. hydroxylated such as alpha hydroxy or beta hydroxy derivatives. The corresponding alcohols, triglycerides and phospholipids of any of those acids are also suitable for use in the present invention. Preferable derivatives include those derived from substitution of the carboxyl group of the acid, such as esters (e.g. triglyceride esters, monoglyceride esters, diglyceride esters, phosphoesters), amides (e.g. ceramide derivatives), salts (e.g. alkali metal and alkali earth metal salts, ammonium salts). In the case of triglyceride ester derivatives, all positional isomers on the glycerol backbone are included.

Oils that are rich in fatty acid triglyceride are thus also suitable for use in the present invention. Such oils are commercially available and include coriander seed (rich in petroselinic acid), parsley seed oil (rich in petroselinic acid), evening primrose oil, (rich in gamma linolenic acid), borage seed oil (rich in gamma linolenic acid), Shea butter (rich in oleic and linoleic acid), fish oils and their concentrates (rich in DHA and EPA), cramb oil (rich in erucic acid) linseed oil (rich in alpha linolenic acid), almond oil (rich in oleic acid) and cotton seed oil (rich in linoleic acid).

Preferable PPAR α activators according to the invention are 12-hydroxystearic acid, cis parinaric acid, trans-7-octadecenoic acid, cis 5,8,11,14,17 eicosapentanoic acid, cis-4,7,10,13,16,19 docosahexenoic acid, cojugated linoleic acid (c9,t11), columbinic acid, linolenelaidic acid, ricinolaidic acid, stearidonic acid, 2-hydroxystearic acid, alpha-linolenic acid, arachidonic acid, cis-11,14-eicosadienoic acid, conjugated linoleic (t10,c12), conjugated linoleic acid (t9,t11), conjugated linoleic acid (50:50 mix of c9, t11 and t10 c12), coriander acids, linolelaidic acid, monopetroselinic acid, petroselinic acid, ricinoleic acid, stearolic acid, thuja extract and trans vaccenic acid.

Further suitable preferred PPAR α activators include cis-11,14,17 eicosatrienoic acid, cis-5 eicosenoic acid, cis-8,11,14 eicosatrienoic acid, hexadecatrienoic acid, palmitoleic acid, petroselaidic acid, trans trans farnesol, cis 13, 16 docosadienoic acid, cis vaccenic acid, cis-11 eicosenoic acid, cis-13,16,19 docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, petroselinyl alcohol, phytanic acid, pinolenic acid, trans-13-octadecenoic acid, tridecyl salicylic acid (TDS).

A further suitable category of PPAR α activators include plant extracts, such as biochanin A (red clover phytoestrogen), chromolaena odorata extract, pomegranate saponifiable hydrolysable extract, buglossoides (stearidonic plant extract), and zanthalene (extract from Sichuan peppercorn).

Particularly preferred lipids, due to their superior anti-ageing effects when combined with petroselinic acid and or DHA (or derivatives thereof) in accordance with the present invention, are selected from the group comprising polyunsaturated fatty acids such linoleic acid, conjugated linoleic acid, linolenic acid eicosatetraynoic acid, arachidonic acid, eicosapentaenoic acid (EPA), docosahexaenoic (DHA) acid (for DHA, only where the first lipid of the inventive composition is PA or derivatives thereof), monounsaturated fatty acids such as petroselinic acid (for PA only where the first lipid of the inventive composition is DHA or derivatives thereof), elaidic acid, oleic acid, erucic acid, and dioic acids such hexadecanedioc acid.

It should also be understood that the PPAR α activator which is present in compositions according to the invention is ideally present in the "active" form; that is, it is not esterified. As such, whilst natural sources of the material such as oils are referred to above, the PPAR α activator which is used in compositions according to the invention is preferably not the raw, esterified form of the activator, but rather a raw material source which is either rich in the unesterified PPAR α activator, or one in which the esterified form has been hydrolysed to release the fatty acid.

The second lipid component is employed in the inventive composition in an amount of between 0.0001% and 50% by weight of the composition. More preferably the amount is from 0.01% to 10% and most preferably from 0.1% to 5% in order to maximise benefits at a minimum cost.

Dermatologically Acceptable Vehicle

The composition used according to the invention also comprises a dermatologically/cosmetically acceptable vehicle to act as a dilutant, dispersant or carrier for the actives. The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the actives, other specific skin-benefit actives such as sunscreens, skin-lightening agents, skin tanning agents may also be included. The vehicle may also further include adjuncts such as antioxidants, perfumes, opacifiers, preservatives, colourants and buffers.

Product Preparation, Form, Use and Packaging

To prepare the topical composition used in the method of the present invention, the usual manner for preparing skin care products may be employed. The active components are generally incorporated in a dermatologically/cosmetically acceptable carrier in conventional manner. The active components can suitably first be dissolved or dispersed in a portion of the water or another solvent or liquid to be incorporated in the composition. The preferred compositions are oil-in-water or water-in-oil or water-in-oil-in-water emulsions.

The composition may be in the form of conventional skin-care products such as a cream, gel or lotion, capsules or the like. The composition can also be in the form of a so-called "wash-off" product, e.g. a bath or shower gel, possibly containing a delivery system for the actives to promote adherence to the skin during rinsing. Most preferably the product is a "leave-on" product; that is, a product to be applied to the skin without a deliberate rinsing step soon after its application to the skin.

The composition may packaged in any suitable manner such as in a jar, a bottle, tube, roll-ball, or the like, in the conventional manner. It is also envisaged that the inventive compositions could be packaged as a kit of two separate compositions, one containing the first lipid component petroselinic acid and/or DHA the second containing the second lipid component of the present invention, to be applied to the skin simultaneously or consecutively.

The composition according to the invention may also be formulated into a form suitable for oral ingestion such as a capsule, tablet or similar.

The method of the present invention may be carried out one or more times daily to the skin which requires treatment. The improvement in skin appearance will usually become visible after 3 to 6 months, depending on skin condition, the concentration of the active components used in the inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

In order that the present invention may be more readily understood, the following examples are given, by way of illustration only.

EXAMPLES

Example 1

Assay to Identify Lipids which Activate PPAR Alpha

An established and widely accepted method by which PPAR activation can be demonstrated and thus by which activators of PPARs can be identified is the reporter gene assay. The protocol is outlined by Kliewer et al. (1992) Nature, 358, 771–774.

This assay is performed on cell lines (e.g. COS or CV-1) which display low endogenous levels of PPAR expression. These cells are plated in a multi-well format and simultaneously transfected with 4 mammalian expression plasmids. These plasmids contain DNA encoding one of the following:

a) the PPAR of interest, in this case PPAR sub type α b) the retinoid X receptor (hereinafter referred to as RXR), RXR sub type a in the case of skin c) a reporter gene such as luciferase or chloramphenicol acetyl transferase (CAT) with a PPAR responsive element inserted into its promoter d) a constitutively expressed reporter gene such as β-galactosidase which is unresponsive to PPAR activation.

Activation of the transfected RXR/PPAR complex by exogenous reagents is determined by measuring the expression of the PPAR responsive reporter gene (luciferase or CAT). This is achieved using commercially available kits such as Luciferase Assay System (Promega) or CAT Enzyme Assay System (Promega). Expression of the PPAR unresponsive reporter gene is similarly measured using commercially available kits such as β-Galactosidase Enzyme Assay System (Promega) and is used as a control to determine the efficiency of transfection and thereby normalise the assay.

In this manner those exogenous lipids which cause expression of luciferase or CAT, preferably which cause a minimum 2-fold increase in luciferase or CAT expression, are readily identifiable as lipids which activate PPAR α.

Example 2

This example demonstrates the anti-ageing benefits of the active ingredients of the present invention.

Procedure for Measuring Procollagen-I Synthesis in Human Dermal Fibroblasts

Preparation of Dermal Fibroblast Conditioned Medium

Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours.

This fibroblast conditioned medium was either analysed immediately or snap frozen in liquid nitrogen and stored at −70° C. for future analysis. The cells were then counted and data from the dot-blot analysis subsequently standardised to cell number.

Dot Blot Assay for Procollagen-I Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes.

A standard for the assay was generated by serial dilution of neat fibroblast conditioned medium from fibroblasts seeded at 10000 cells/cm$^2$ in a 175 cm$^2$ flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 μl of medium was applied per well. The medium was allowed to filter through the membrane under gravity (30 minutes) after which the membrane was washed twice with PBS (200 μl). These PBS washes were allowed to filter through the membrane under gravity (2×15 minutes).

The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for procollagen-I analysis were blocked with 5% (w/v) non-fat dried milk powder/0.05% Tween 20 in PBS. The following day, the membranes were probed with 1:10000 dilution of primary antibodies to human procollagen-I (MAB1912; rat monoclonal; Chemicon Int. Inc., Temecula, Calif.) for 2 hours at room temperature. The membranes were subsequently washed with TBS/0.05% Tween 20 (3×5 minutes) and then incubated with 1:1000 dilution of $^{125}$I-conjugated anti-rat fragments (Amersham) as required for 1 hour at room temperature. Following this the Immobilon strips were again washed with TBS/Tween 20 (3×5 minutes) before being allowed to dry in air at room temperature.

The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents procollagen-I synthesis were determined relative to a vehicle treated control value of 100 arbitrary units.

Tests

The table 1 below indicates the synergistic effect of petroselinic acid/DHA in combination with linoleic acid on procollagen-I synthesis in human dermal fibroblasts, and the amounts in which the actives were applied. In order to normalise the results the effects of the test substances were determined relative to a vehicle treated control value of 100 arbitrary units. A comparative test was performed with a combination of lipids outside the scope of the present invention, oleic acid in combination with linoleic acid. The concentrations of reagents used in the trials had no influence on cell viability.

TABLE 1

| Treatment | Procollagen-I |
|---|---|
| Control (Vehicle) | 100 |
| 1 μM PA | 87.6 |
| 10 μM linoleic acid | 110.3 |
| 1 μM PA + 10 μM linoleic acid | 152.2 |
| 10 μM DHA | 105.1 |
| 10 μM linoleic acid | 111.8 |
| 10 μM DHA + 10 μM linoleic acid | 129.8 |
| 10 μM oleic acid | 102.6 |
| 1 μM linoleic acid | 99.3 |
| 10 μM oleic acid + 1 μM linoleic acid | 89.5 |

The results in table 1 demonstrate that the specific combination of petroselinic acid or DHA with a lipid PPAR alpha activator (a combination within the scope of the present invention) surprisingly synergistically promotes the synthesis of procollagen-I in human dermal fibroblasts which is a known anti-ageing marker. In contrast, the combination of oleic acid (which is a lipid that is structurally closely related to petroselinic acid) and a lipid PPAR alpha activator (a combination outside the scope of the present invention) does not exhibit such a synergistic effect.

The boosting or maintenance of the level of procollogen 1 in skin is associated with many skin anti-ageing benefits such as wrinkle effacement and dermal repair of photodamaged skin.

Example 3

The formulation below describes an oil in water cream suitable for the methods and uses according to the present invention. The percentages indicated are by weight of the composition.

| | wt % | Wt % | Wt % |
|---|---|---|---|
| Mineral Oil | 4 | 4 | 4 |
| Petroselinic acid (triglyceride) ex NU Check Prep | 1.15 | 2 | 3 |
| Linoleic acid triglyceride ex NU Check Prep | 0 | 2 | 0 |
| Linolenic acid triglyceride ex NU Check Prep | 0 | 0 | 3 |
| Conjugated linoleic acid triglyceride ex Loders Croklaan | 0.5 | 0 | 0 |
| Brij 56* | 4 | 4 | 4 |
| Alfol 16RD* | 4 | 4 | 4 |
| Triethanolamine | 0.75 | 0.75 | 0.75 |
| Butane-1,3-diol | 3 | 3 | 3 |
| Xanthan gum | 0.3 | 0.3 | 0.3 |
| Perfume | Qs | qs | qs |
| Butylated hydroxy toluene | 0.01 | 0.01 | 0.01 |
| Water | to 100 | to 100 | To 100 |

*Brij 56 is cetyl alcohol POE (10)
Alfol 16RD is cetyl alcohol

Example 4

In the composition of example 3 above, the petroselinic acid (triglyceride) is replaced with DHA (triglyceride) ex NU Check Prep.

Example 5

The formulation below describes an emulsion cream according to the present invention.

| FULL CHEMICAL NAME OR CTFA NAME | TRADE NAME | WT. % | WT. % | WT % |
|---|---|---|---|---|
| Coriander seed oil ex Loders Croklaan (PA triglyceride 60–75% of total fatty acids) | | 2.0 | 3 | 1.5 |
| Borage seed oil ex Brooks | | 1 | 0 | 0 |
| Shea butter ex Capital City | | 0 | 2 | |
| Evening Primrose Oil ex Brooks | | 0 | 0 | 1.5 |
| Disodium EDTA | Sequesterene Na2 | 0.05 | 0.05 | 0.05 |
| Magnesium aluminium silicate | Veegum Ultra | 0.6 | 0.6 | 0.6 |
| Methyl paraben | Methyl Paraben | 0.15 | 0.15 | 0.15 |
| Simethicone | DC Antifoam Emulsion | 0.01 | 0.01 | 0.01 |
| Butylene glycol 1,3 | Butylene Glycol 1,3 | 3.0 | 3.0 | 3.0 |
| Hydroxyethylcellulose | Natrosol 250HHR | 0.5 | 0.5 | 0.5 |
| Glycerine, USP | Glycerine USP | 2.0 | 2.0 | 2.0 |
| Xanthan gum | Keltrol 1000 | 0.2 | 0.2 | 0.2 |
| Triethanolamine | Triethanolamine (99%) | 1.2 | 1.2 | 1.2 |
| Stearic acid | Pristerene 4911 | 3.0 | 3.0 | 3.0 |
| Propyl paraben NF | Propylparaben NF | 0.1 | 0.1 | 0.1 |
| Glyceryl hydrostearate | Naturechem GMHS | 1.5 | 1.5 | 1.5 |
| Stearyl alcohol | Lanette 18 DEO | 1.5 | 1.5 | 1.5 |
| Isostearyl palmitate | Protachem ISP | 6.0 | 6.0 | 6.0 |
| C12–15 alcohols octanoate | Hetester FAO | 3.0 | 3.0 | 3.0 |
| Dimethicone | Silicone Fluid 200 (50 cts) | 1.0 | 1.0 | 1.0 |
| Cholesterol NF | Cholesterol NF | 0.5 | 0.5 | 0.5 |
| Sorbitan stearate | Sorbitan Stearate | 1.0 | 1.0 | 1.0 |
| Butylated hydroxytoluene | Embanox BHT | 0.05 | 0.05 | 0.05 |
| Tocopheryl acetate | Vitamin E Acetate | 0.1 | 0.1 | 0.1 |
| PEG-100 stearate | Myrj 59 | 2.0 | 2.0 | 2.0 |
| Sodium stearoyl lactylate | Pationic SSL | 0.5 | 0.5 | 0.5 |
| Hydroxycaprylic acid | Hydroxycaprylic Acid | 0.1 | 0.1 | 0.1 |
| Alpha-bisabolol | Alpha-bisabolol | 0.2 | 0.2 | 0.2 |
| Water, DI | | q.s. to 100 | q.s. to 100 | q.s. to 100 |

Example 6

In the compositions of example 5 above, the coriander seed oil is replaced with Fish oil ex Ross.

The above topical compositions provide an effective cosmetic treatment to improve the appearance of wrinkled, aged, photodamaged skin when applied to normal skin that has lost its smoothness and firmness through the normal aging process or when applied to youthful skin to help prevent or delay such undesirable changes. The compositions can be processed in conventional manner.

What is claimed is:

1. A topical composition for treating skin aging comprising:

(a) a first lipid selected from the group consisting of petroselinic acid and derivatives thereof;

(b) a second lipid selected from the group consisting of linoleic acid, conjugated linoleic acid, and mixtures thereof; and (c) a dermatologically acceptable vehicle.

2. The topical composition of claim 1, wherein said second lipid is present in amounts of about 0.1 % to about 5 % by weight of said composition.

3. The topical composition of claim 1, wherein said second lipid is conjugated linoleic acid (c9,t11), conjugated linoleic acid (t10,c12), conjugated linoleic acid (t9,t11), or conjugated linoleic acid (50:50 mix of c9 t11 and t10 c12).

4. The topical composition of claim 1, wherein said second lipid is in the free and unconjugated form.

5. The topical composition of claim 1, wherein the composition is provided in the form of a kit comprising two separate compositions, the first composition comprising said first lipid and the second composition comprising said second lipid.

* * * * *